(12) United States Patent
Aasberg-Petersen et al.

(10) Patent No.: US 11,370,660 B2
(45) Date of Patent: Jun. 28, 2022

(54) METHOD FOR THE PREPARATION OF SYNTHESIS GAS

(71) Applicant: Haldor Topsøe A/S, Kgs. Lyngby (DK)

(72) Inventors: Kim Aasberg-Petersen, Allerød (DK); Pat A. Han, Smørum (DK)

(73) Assignee: Topsoe A/S, Kgs. Lyngby (DK)

( * ) Notice: Subject to any disclaimer, the term of this patent is extended or adjusted under 35 U.S.C. 154(b) by 0 days.

(21) Appl. No.: 16/623,835

(22) PCT Filed: Jul. 20, 2018

(86) PCT No.: PCT/EP2018/069776
§ 371 (c)(1),
(2) Date: Dec. 18, 2019

(87) PCT Pub. No.: WO2019/020513
PCT Pub. Date: Jan. 31, 2019

(65) Prior Publication Data
US 2020/0131034 A1     Apr. 30, 2020

(30) Foreign Application Priority Data

Jul. 25, 2017  (DK) .......................... PA 2017 00425
Sep. 25, 2017  (DK) .......................... PA 2017 00522
May 28, 2018  (DK) .......................... PA 2018 00237
Jul. 6, 2018   (DK) .......................... PA 2018 00351

(51) Int. Cl.
  *C01B 3/38*    (2006.01)
  *C01B 13/02*   (2006.01)
  *C07C 29/151*  (2006.01)
  *C10K 3/06*    (2006.01)

(52) U.S. Cl.
  CPC .............. *C01B 3/382* (2013.01); *C01B 3/384* (2013.01); *C01B 13/0229* (2013.01); *C07C 29/1518* (2013.01); *C10K 3/06* (2013.01); *C01B 2203/0244* (2013.01); *C01B 2203/0261* (2013.01); *C01B 2203/061* (2013.01)

(58) Field of Classification Search
  CPC ... C01B 3/382; C01B 3/384; C01B 2203/061; C01B 2203/0261; C01B 2203/0244; C01B 13/0229; C10K 3/06; C07C 29/1518; Y02E 50/30; Y02E 60/36; Y02P 20/133; C25B 1/04
  See application file for complete search history.

(56) References Cited

U.S. PATENT DOCUMENTS

| | | | |
|---|---|---|---|
| 4,479,925 | A | 10/1984 | Shires et al. |
| 4,792,441 | A | 12/1988 | Wang et al. |
| 10,889,496 | B2 | 1/2021 | Aasberg-Petersen et al. |
| 11,053,130 | B2 | 6/2021 | Han |
| 11,124,424 | B2 | 9/2021 | Han |
| 2003/0065042 | A1 | 4/2003 | Shaw |
| 2004/0063798 | A1* | 4/2004 | Erikstrup ................ C01B 3/382 518/704 |
| 2004/0182002 | A1 | 9/2004 | Malhotra et al. |
| 2005/0234278 | A1* | 10/2005 | van Egmond ....... F25J 3/04157 585/324 |
| 2007/0256360 | A1 | 11/2007 | Kindig et al. |
| 2007/0299144 | A1 | 12/2007 | Davey et al. |
| 2009/0165459 | A1 | 7/2009 | Henriksen et al. |
| 2009/0314994 | A1 | 12/2009 | Filippi et al. |
| 2010/0076097 | A1 | 3/2010 | Metz et al. |
| 2012/0091730 | A1 | 4/2012 | Stuermer et al. |
| 2012/0100062 | A1 | 4/2012 | Nakamura et al. |
| 2013/0072583 | A1 | 3/2013 | Koskinen et al. |
| 2013/0252299 | A1 | 9/2013 | Bell et al. |
| 2013/0345325 | A1* | 12/2013 | Lecomte ............ C07C 29/1518 518/702 |
| 2014/0323597 | A1* | 10/2014 | Stuckert .............. B01J 19/2475 518/703 |
| 2014/0357736 | A1 | 12/2014 | Dahl |
| 2016/0115405 | A1 | 4/2016 | Zubrin et al. |
| 2017/0002281 | A1* | 1/2017 | Aasberg-Petersen ..... C01B 3/38 |
| 2020/0109051 | A1 | 4/2020 | Aasberg-Petersen et al. |
| 2020/0172394 | A1 | 6/2020 | Han et al. |

FOREIGN PATENT DOCUMENTS

| | | |
|---|---|---|
| CN | 101892492 A | 11/2010 |
| EP | 0 999 178 A1 | 5/2000 |
| EP | 2 166 064 A1 | 3/2010 |
| EP | 2 192 082 A1 | 6/2010 |
| EP | 2 589 574 A1 | 5/2013 |
| EP | 2 676 924 A1 | 12/2013 |
| EP | 2 805 914 B1 | 9/2017 |
| GB | 2545474 A | 6/2017 |
| KR | 10-2005-0075628 A | 7/2005 |
| WO | WO 2007/049069 A1 | 5/2007 |
| WO | WO 2010/008494 A1 | 1/2010 |
| WO | WO 2011/088981 A1 | 7/2011 |
| WO | WO 2012/084135 A1 | 6/2012 |
| WO | WO 2015/067436 A1 | 5/2015 |
| WO | WO 2015/128456 A1 | 9/2015 |
| WO | WO 2016/008820 A1 | 1/2016 |

* cited by examiner

OTHER PUBLICATIONS

K.H. Kaggerud et al., "Chemical and Process Integration: Synergies in Co-Production of Power and Chemicals from Natural Gas with $CO_2$ Capture." Applied Thermal Engineering, vol. 26, pp. 1345-1352 (2006).

*Primary Examiner* — Anthony J Zimmer
*Assistant Examiner* — Syed T Iqbal
(74) *Attorney, Agent, or Firm* — Blank Rome LLP

(57) ABSTRACT

Method for the preparation of synthesis gas based on a combination of the ATR process or partial oxidation of hydrocarbon fee stock using oxygen from the electrolysis of water and an air separation unit to produce the synthesis gas.

9 Claims, No Drawings

METHOD FOR THE PREPARATION OF SYNTHESIS GAS

The present application is directed to the preparation of synthesis gas. More particular, the invention combines air separation, electrolysis of water and partial oxidation of a hydrocarbon feed stock in the preparation of a hydrogen and carbon oxides containing synthesis gas.

Production of synthesis gas e.g. for the methanol synthesis with natural gas feed is typically carried out by steam reforming.

The principal reaction of steam reforming is (given for methane):

$$CH_4 + H_2O \leftrightarrows 3H_2 + CO$$

Similar reactions occur for other hydrocarbons. Steam reforming is typically accompanied by the water gas shift reaction:

$$CO + H_2O \leftrightarrows CO_2 + H_2$$

Steam reforming can e.g be done by, a combination of a tubular reformer (also called steam methane reformer, SMR) and autothermal reforming (ATR), also known as primary and secondary reforming or 2-step reforming. Alternatively, stand-alone SMR or stand-alone ATR can be used to prepare the synthesis gas.

The main elements of an ATR reactor are a burner, a combustion chamber, and a catalyst bed contained within a refractory lined pressure shell. In an ATR reactor, partial oxidation or combustion of a hydrocarbon feed by substoichio-metric amounts of oxygen is followed by steam reforming of the partially combusted hydrocarbon feed stream in a fixed bed of steam reforming catalyst. Steam reforming also takes place to some extent in the combustion chamber due to the high temperature. The steam reforming reaction is accompanied by the water gas shift reaction. Typically, the gas is at or close to equilibrium at the outlet of the ATR reactor with respect to steam reforming and water gas shift reactions. The temperature of the exit gas is typically in the range between 850 and 1100° C. More details of ATR and a full description can be found in the art such as "Studies in Surface Science and Catalysis, Vol. 152, "Synthesis gas production for FT synthesis"; Chapter 4, p. 258-352, 2004". In the same reference additional information can be found regarding steam reforming (SMR) and 2-step reforming.

Regardless of whether stand-alone SMR, 2-step reforming, or stand-alone ATR is used, the product gas will comprise hydrogen, carbon monoxide, and carbon dioxide as well as other components normally including methane and steam.

An alternative for production of synthesis gas is by partial oxidation alone also known as PDX. The main elements of a PDX reactor are a burner and a combustion chamber contained within a refractory lined pressure shell. In a PDX reactor, partial oxidation or combustion of a hydrocarbon feed by substoichiometric amounts of oxygen takes place. Some steam reforming also takes place and the water gas shift reaction is active. The exit temperature from the reactor is typically 1100-1500° C. Some soot formation may take place in the reactor and the soot may need to be removed downstream the PDX reactor.

Methanol synthesis gas preferably has a composition corresponding to a so-called module ($M=(H_2-CO_2)/(CO+CO_2)$) of 1.90-2.20 or more preferably slightly above 2 (eg. 2.00-2.10).

Steam reforming in an SMR typically results in a higher module i.e. excess of hydrogen, while 2-step reforming can provide the desired module. In 2-step reforming the exit temperature of the steam reformer is typically adjusted such that the desired module is obtained at the outlet of the ATR. For standalone ATR, the module in the ATR exit gas is often lower than desired when the synthesis gas is used for methanol production. This can for example be rectified by removal of carbon dioxide or by recovering hydrogen from the purge gas from the methanol synthesis loop. In both cases, the methanol loop efficiency is lower than what is obtained by 2-step reforming.

In 2-step reforming the steam methane reformer (SMR) must be large and a significant amount of heat is required to drive the endothermic steam reforming reaction. Hence, it is desirable if the size and duty of the steam reformer can be reduced. Furthermore, the ATR in the 2-step reforming concept requires oxygen. Today this is typically produced in a cryogenic air separation unit (ASU). The size and cost of this ASU is large. If part or all the oxygen could be produced by other means, this would be desirable.

Thus, this invention provides a method for the preparation of synthesis gas comprising the steps of:
(a) separating atmospheric air into a separate oxygen containing stream and into a separate nitrogen containing stream;
(b) preparing a separate hydrogen containing stream and a separate oxygen containing stream by electrolysis of water and/or steam;
(c1) partial oxidizing or autothermal reforming at least a part of a hydrocarbon feed stock with at least a part of the oxygen containing stream obtained by the separation of atmospheric air in step (a) and at least a part of the oxygen containing stream obtained by the electrolysis of water in step (b) to a process gas comprising hydrogen, carbon monoxide and carbon dioxide; or
(c2) gasifying coal or biomass with water and at least a part of the oxygen containing stream obtained by the separation of atmospheric air in step (a) and at least a part of the oxygen containing stream obtained by the electrolysis of water in step (b) to a process gas comprising hydrogen, carbon monoxide and carbon dioxide; and
(d) introducing at least part of the separate hydrogen containing stream from step (b) into the process gas from step (c1) or (c2).

The method for air separation employed in the method according to the invention is preferably fractional distillation in a cryogenic air separation unit to provide a part of the oxygen for use in step (c1) or (c2). Alternatively, other methods such as membrane separation, pressure swing adsorption (PSA) and vacuum pressure swing adsorption (VPSA) can be utilized.

Alternative to the partial oxidizing or the autothermal reforming at least a part of a hydrocarbon feed stock, a process gas containing hydrogen, carbon monoxide and carbon dioxide can be produced by gasifying a solid carbonaceous feed stock, preferably coal or biomass, utilizing the oxygen stream formed in the air separation together with the oxygen from the electrolysis of water and/or steam.

In an embodiment of the invention, the hydrocarbon feed stock in step (c1) is partly steam reformed in a primary reformer (SMR) upstream the autothermal reformer.

In one embodiment using a hydrocarbon feed stock, the electrolysis unit is operated such that all the hydrogen produced in this unit is added in step (d) to the process gas from step (c1) and the module of the resulting mixture of this hydrogen and the process gas from step (c1) is between 1.9 and 2.2 or preferably between 2 and 2.1.

In this embodiment some or preferably all the oxygen from the electrolysis unit is added to the autothermal reformer in step (c1).

Additionally, the ATR can be supplemented by a heat exchange reformer arranged either in series or in parallel with the ATR.

A heat exchange reformer is alternatively called a gas heated reformer and heat exchange reforming may be called gas heated reforming.

In the series concept, part or all the hydrocarbon feedstock is directed to the heat exchange reformer in which steam reforming takes place. The remaining part of the hydrocarbon feedstock can be bypassed the heat exchange reformer and introduced into the autothermal reformer.

Thus, in an embodiment of the invention, the method comprises the further step of steam reforming part or the entire hydrocarbon feed stock in indirect heat transfer relationship with part or all the process stream leaving the autothermal reforming step (c1).

Typically, the gas leaving the heat exchange reformer in series will be at or close to equilibrium at a temperature of 650-800° C. The exit gas from the heat exchange reformer in series is then directed to the ATR together with any hydrocarbon feed which was not steam reformed in the heat exchange reformer. Part or all the exit gas from the ATR is used as heat source in the heat exchange reformer by heat exchange to drive the endothermic steam reforming reaction.

In the parallel concept of the heat exchange reforming, part of the hydrocarbon feedstock is directed to the ATR and the remaining hydrocarbon feed stock and/or a second hydrocarbon feed stock to the heat exchange reformer.

The feed stocks to the ATR and to the heat exchange reformer may have different compositions, e.g. different steam to carbon ratios.

In the heat exchange reformer in the parallel concept steam reforming takes place. Part or all the exit gas from the ATR is utilized as heat source in the heat exchange reformer by heat exchange to drive the endothermic steam reforming reaction.

The gas leaving the catalyst in the heat exchange reformer may optionally be mixed with part or the entire the exit gas from the ATR before the latter is used as heat source. Alternatively, the exit gas from the heat exchange reformer and the exit gas from the ATR can be mixed downstream the heat exchange reformer.

Thus, in further an embodiment of the invention, the method comprises the further step of steam reforming a part of the hydrocarbon feed stock and/or a second hydrocarbon feed stock in indirect heat transfer relationship with part or all the process stream leaving the autothermal reforming step (c1) and mixing the heat exchange steam reformed process gas with autothermal reformed process gas.

There is also the possibility of not mixing the two gases depending on the final use(s) of the synthesis gas.

Irrespective of whether a parallel or a series concept of the heat exchange reformer is used, the operating parameters and the heat exchange reformer design can in principle be adjusted to give a module M of the desired value of 1.9-2.2 or preferably 2.0-2.1, in particular when using the synthesis gas for the preparation of methanol.

However, the size of the heat exchange reformer may render such a solution uneconomical. In such scenario, the use of hydrogen from the electrolysis as described above may prove beneficial. This allows a smaller heat exchange reformer reactor.

The amount of hydrogen can be tailored such that when the hydrogen is mixed with the process gas generated by the reforming steps, the desired value of M (between 1.90 and 2.20 or preferably between 2.00 and 2.10) is achieved.

The module can additionally be adjusted to the desired value by addition of essentially pure carbon dioxide to the hydrocarbon feed stock and/or to the synthesis gas, and/or upstream the autothermal reformer.

Thus, in an embodiment of the invention, wherein essentially pure carbon dioxide is added to the hydrocarbon feed stock upstream of the autothermal reforming.

The electrolysis at the same time produces oxygen, which is fed to the ATR or the PDX. This reduces the size of the secondary oxygen supply, as e.g. an air separation unit (ASU).

If the power for the electrolysis is produced (at least in part) by sustainable sources, the $CO_2$-emissions from the plant per unit of product produced is reduced.

In all of the above cases, the feed stock may initially be subjected to the steps of purification (including desulphurization) and adiabatic pre-reforming.

Preferably, the hydrocarbon feed stock comprises natural gas, methane, LNG, naphtha or mixtures thereof either as such or pre-reformed and/or desulfurized.

The hydrocarbon feed stock may further comprise hydrogen and/or steam as well as other components.

The invention can further be employed for producing synthesis gas for other applications where it is desirable to in-crease the hydrogen concentration in the feed gas and where part of the oxygen needed for synthesis gas production is favorably produced by electrolysis.

The electrolysis may be performed by various means known in the art such as by solid oxide based electrolysis or electrolysis by alkaline cells or polymer cells (PEM).

EXAMPLE

Comparison Between Conventional ATR and ATR+Electrolysis According to the Invention

| Comparison Table | | |
|---|---|---|
|  | ATR | ATR + electrolysis |
| ATR inlet T [° C.] (feed) | 625 | 625 |
| ATR inlet T (Oxidant) | 240 | 240 |
| ATR outlet T [° C.] | 1050 | 1050 |
| ATR inlet P [kg/cm² g] | 31 | 31 |
| ATR outlet flow [Nm³/h] | 93934 | 90667 |
| Feed to ATR | | |
| H2 [Nm³/h] | 3345 | 3228 |
| CO2 [Nm³/h] | 698 | 673 |
| CH4 [Nm³/h] | 24103 | 23265 |
| CO [Nm³/h] | 16 | 15 |
| H2O [Nm³/h] | 18442 | 17801 |
| Oxidant to ATR | | |
| H2O [Nm³/h] | 131 | 127 |
| N2 [Nm³/h] | 278 | 268 |
| O2 [Nm³/h] | 13601 | 13128 |
| Electrolysis product | | |
| H2 [Nm³/h]* | 0 | 2434 |
| O2 [Nm³/h]** | 0 | 1217 |

-continued

| Comparison Table | | |
|---|---|---|
|  | ATR | ATR + electrolysis |
| Oxygen from ASU | | |
| O2 [Nm³/h] | 13601 | 11911 |
| Product gas | | |
| H2 [Nm³/h] | 49874 | 50573 |
| CO2 [Nm³/h] | 4047 | 3907 |
| CH4 [Nm³/h] | 643 | 621 |
| CO [Nm³/h] | 20127 | 19427 |
| H2O [Nm³/h] | 18965 | 18306 |
| N2 [Nm³/h] | 278 | 268 |
| Module | 1.90 | 2.00 |

*Included in product gas
**Included in oxidant to ATR

As apparent from the Comparison Table above, the inlet and outlet flow from the ATR is less when applying electrolysis. That is that the ATR reactor is smaller in the method according to the invention. The same is true as regards the ASU.

Another advantage of the method according to the invention is that the required feed amount to the ATR is less and the module of the synthesis gas is improved if the synthesis gas is used for methanol production in the method according to the invention.

The invention claimed is:

1. Method for the preparation of gas for the synthesis of methanol, comprising the steps of:
    (a) separating atmospheric air into a separate oxygen containing stream and into a separate nitrogen containing stream;
    (b) preparing a separate hydrogen containing stream and a separate oxygen containing stream by electrolysis of water and/or steam;
    (c) partial oxidizing or autothermal reforming in an autothermal reformer at least a part of a hydrocarbon feed stock with at least a part of the oxygen containing stream obtained by the separation of atmospheric air in step (a) and at least a part of the oxygen containing stream obtained by the electrolysis of water and/or steam in step (b) to a process gas comprising hydrogen, carbon monoxide and carbon dioxide;
    (d) introducing at least part of the separate hydrogen containing stream from step (b) into the process gas from step (c), wherein the resulting mixture of hydrogen in the separate hydrogen containing stream with the process gas from step (c) form the gas for the synthesis of methanol, the gas having a module M, where $M=(H_2-CO_2)/(CO+CO_2)$, of between 1.9 and 2.2; and
    (e) adjusting the module M by tailoring the amount of hydrogen mixed with the process gas and/or by adding $CO_2$ to the hydrocarbon feed stock upstream of partial oxidizing or autothermal reforming and/or downstream of step (c).

2. The method of claim 1, comprising the further step of steam reforming, in a heat exchange reformer, a part of the hydrocarbon feed stock not reformed in the autothermal reformer, by indirect heat transfer with part or all the process stream leaving the autothermal reforming step (c).

3. The method of claim 1, comprising the further step of steam reforming, in a heat exchange reformer, a part of the hydrocarbon feed stock not reformed in the autothermal reformer and/or a second hydrocarbon feed stock by indirect heat transfer with part or all the process gas leaving the autothermal reforming step (c), and mixing the heat exchange steam reformed process gas with autothermal reformed process gas.

4. The method of claim 1, comprising a further step of primary steam reforming the hydrocarbon feed stock upstream step (c).

5. The method of claim 1, wherein the hydrocarbon feed stock comprises natural gas, methane, LNG, naphtha or mixtures thereof either as such or pre-reformed and/or desulfurized.

6. The method of claim 1, wherein the separating of atmospheric air in step (a) and/or the electrolysis of water and/or steam in step (b) is powered at least in part by renewable energy.

7. The method of claim 1, wherein the separating of atmospheric air in step (a) is performed by cryogenic separation.

8. The method of claim 1, wherein the module M is between 2 to 2.1.

9. The method of claim 1, wherein the gas for the synthesis of methanol is, in a further step, converted to a methanol product.

* * * * *